United States Patent
Kleijnen et al.

(10) Patent No.: US 12,329,628 B2
(45) Date of Patent: Jun. 17, 2025

(54) DELIVERY CATHETER SYSTEM

(71) Applicant: Medtronic, Inc., Minneapolis, MN (US)

(72) Inventors: Patrick Kleijnen, Mheer (NL); Niels van der Knaap, Maastricht (NL); Estelle Fraysse, Eindhoven (NL)

(73) Assignee: MEDTRONIC, INC., Minneapolis, MN (US)

( * ) Notice: Subject to any disclaimer, the term of this patent is extended or adjusted under 35 U.S.C. 154(b) by 311 days.

(21) Appl. No.: 17/849,656

(22) Filed: Jun. 26, 2022

(65) Prior Publication Data
US 2023/0000610 A1    Jan. 5, 2023

(30) Foreign Application Priority Data

Jul. 1, 2021  (EP) .................................. 21183092

(51) Int. Cl.
*A61F 2/01*   (2006.01)
*A61M 25/00*   (2006.01)

(52) U.S. Cl.
CPC ......... *A61F 2/013* (2013.01); *A61M 25/0082* (2013.01); *A61F 2002/015* (2013.01)

(58) Field of Classification Search
CPC ........ A61F 2/0105; A61F 2/011; A61F 2/013; A61F 2/014; A61F 2/2433; A61F 2/2436; A61F 2/2466; A61F 2/966; A61F 2/01; A61M 25/0082

USPC ......................................................... 606/200
See application file for complete search history.

(56) References Cited

U.S. PATENT DOCUMENTS

| | | | |
|---|---|---|---|
| 2001/0001114 A1 | 5/2001 | Tsugita et al. | |
| 2007/0123913 A1 | 5/2007 | Beulke et al. | |
| 2016/0317276 A1* | 11/2016 | Groh | A61F 2/013 |
| 2020/0253709 A1* | 8/2020 | Russell | A61F 2/014 |
| 2020/0368006 A1* | 11/2020 | Gale | A61F 2/013 |

FOREIGN PATENT DOCUMENTS

EP      2283892 B1      6/2015

OTHER PUBLICATIONS

Extended European Search Report completed Dec. 9, 2021 in EP Appl. No. 21 18 3092.

* cited by examiner

*Primary Examiner* — Jocelin C Tanner
(74) *Attorney, Agent, or Firm* — Medler Ferro Woodhouse & Mills PLLC

(57) ABSTRACT

A delivery catheter system includes a catheter and an integrated embolic filter that is deployable prior to the delivery of a prosthesis in a patient's vasculature and retrievable after delivery of said prosthesis. The embolic filter is moveable from a collapsed state, in which the embolic filter is retained within the catheter body, to a deployed state in which the embolic filter extends from the catheter body and, in use, into contact with an inner wall of a patient's vasculature.

12 Claims, 8 Drawing Sheets

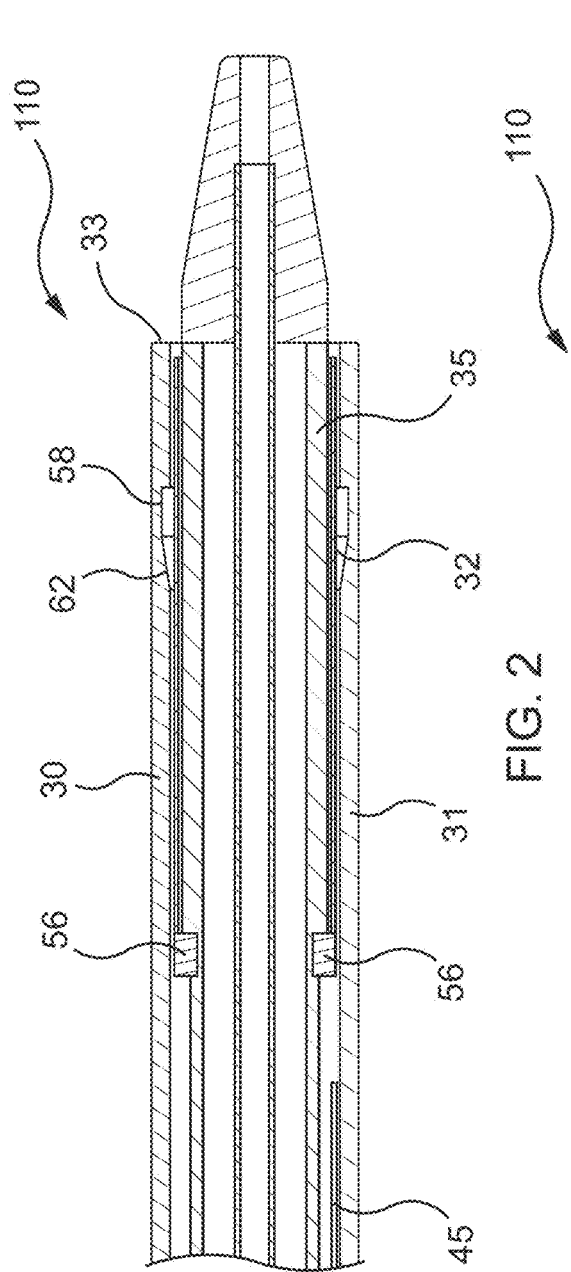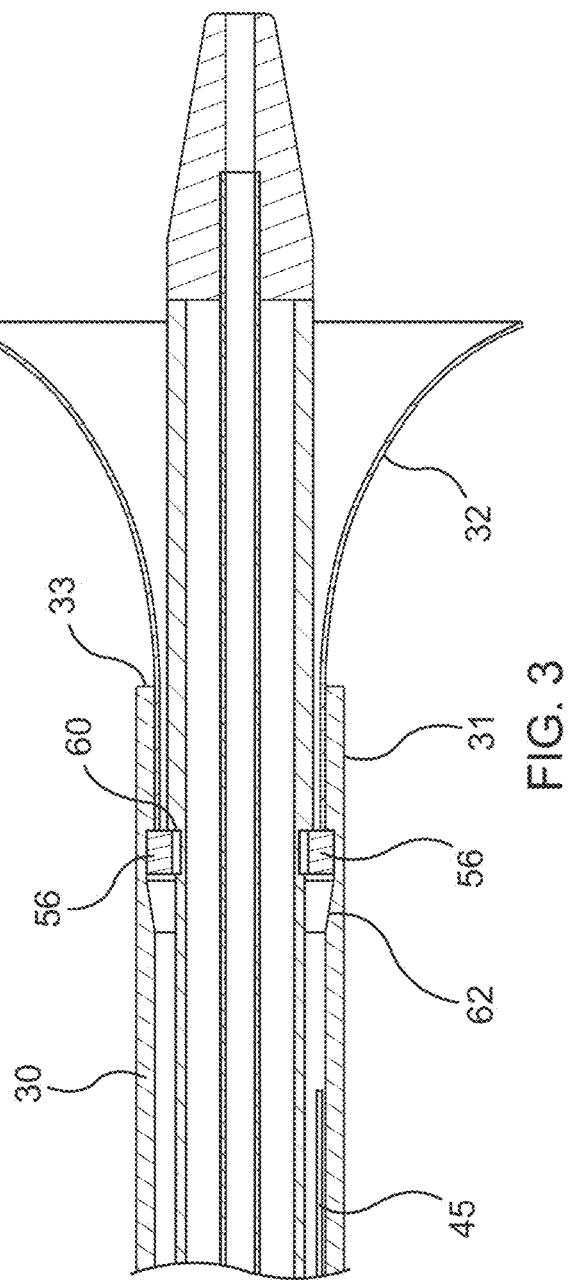
FIG. 2
FIG. 3

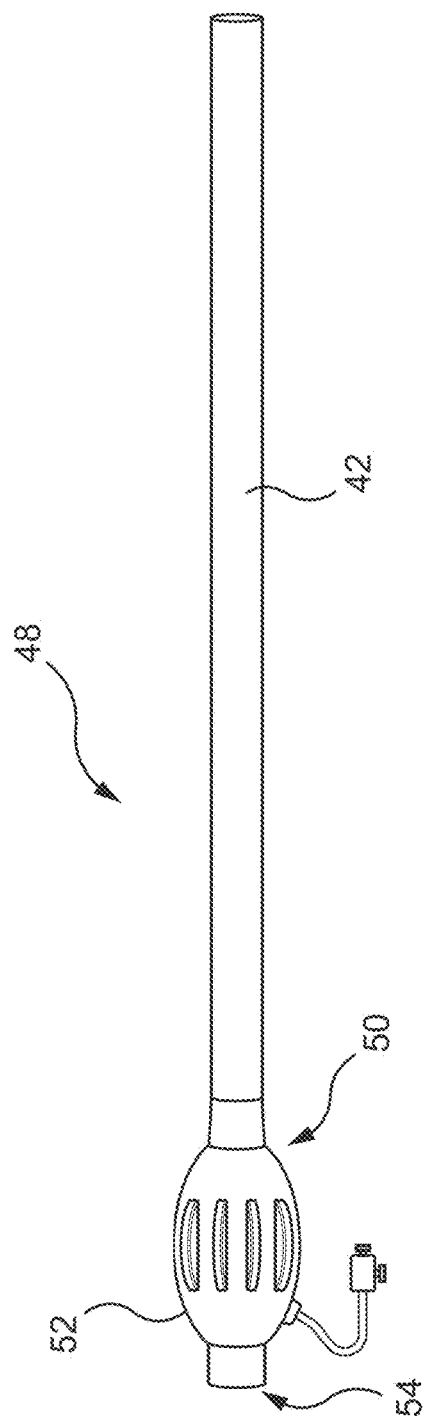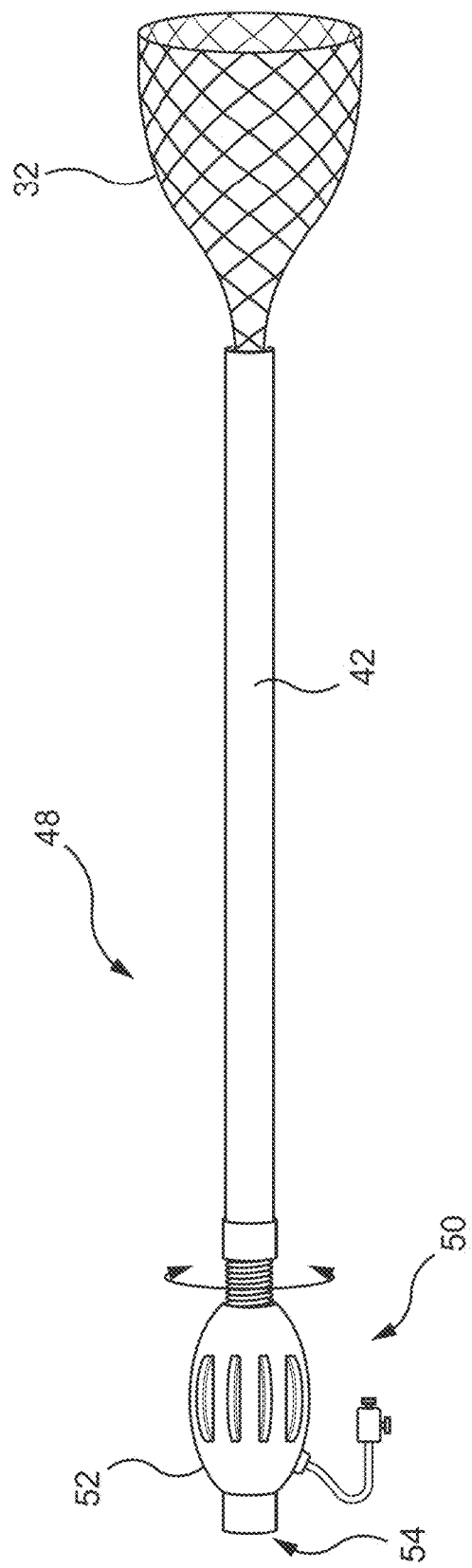

DELIVERY CATHETER SYSTEM

FIELD OF THE INVENTION

The present invention relates to a delivery catheter system.

BACKGROUND

Catheters have long been used for the treatment of diseases of the cardiovascular system, such as treatment or removal of stenosis. More recently, catheters have been used for replacement of heart valves, in particular, the aortic valve in a procedure sometimes known as transcatheter aortic valve implantation (TAVI). TAVI is now the principal therapeutic option in patients with severe aortic stenosis deemed inoperable or at high surgical risk. Over 300,000 TAVI procedures were performed worldwide in 2018, and the mortality benefits of TAVI in inoperable and high-risk surgical patients have been recognised. However, the benefit of TAVI is attenuated by the occurrence of major disabling stroke which is associated with increased mortality and in the short term reduced quality of life. During TAVI, extensive manipulation of the calcified native valve and aortic wall takes place using large-sized catheters and rigid delivery systems. Subsequently, balloon valvuloplasty, positioning and implanting of the valve, and possibly post-dilation, takes place. Consequently, dislodgement and embolization of aortic debris and crushed calcified native valves seems inevitable and can provoke stroke by reaching brain vessels.

Cerebral embolic protection devices have been developed to reduce the risk of stroke by providing an efficient protection of the entire brain. To perform well, the device requires to have a minimum filtering porosity, a good anchoring on the vessel without damaging the vessel and a good stability by withstanding the blood pressure.

Current embolic protection devices on the market/in development include the Boston Scientific Sentinel (RTM) device, the Keystone Heart TriGUARD 3™ device, the Edwards Life Sciences Embrella device, the Emboline Emboliner™ device, and the Innovative Cardiovascular Solutions Emblok™ system. However, all these devices and systems are delivered separately from the delivery TAVI device.

SUMMARY

According to the present invention there is provided a delivery catheter system comprising: a catheter including an elongate catheter body having a distal tip and a capsule containing a deliverable prosthesis; and an integrated embolic filter, the embolic filter deployable prior to the delivery of a prosthesis in a patient's vasculature and retrievable after delivery of said prosthesis, wherein the embolic filter is moveable from a collapsed state, in which the embolic filter is retained within the catheter body, to a deployed state in which the embolic filter extends from the catheter body and, in use, into contact with an inner wall of a patient's vasculature.

Traditionally, embolic filter devices are placed separately from the delivery device which implies an additional step before the procedure. Surgeons need to be implanted first the embolic protection device via the right radial artery. Unexperienced cardiac surgeons do not use cerebral protection device due to the additional time required to implement them. The present arrangement provides an integrated embolic filters, which removes the need for two separate processes.

It will be appreciated that the delivery catheter assembly may be used for a range of different purposes, and the article being delivered will vary accordingly. The delivery catheter assembly may be used to place a stent in a patient's vasculature, and as such the article may be a stent. The delivery catheter assembly may be used for a transcatheter aortic valve implantation, and as such the article may be a replacement valve. Alternatively, the delivery catheter assembly may be used for any type of valve replacement procedure.

The article delivery catheter may be a transcatheter aortic valve implantation (TAVI) delivery catheter, a stent delivery catheter, a tool delivery catheter any other type of valve delivery catheter.

The embolic filter may be retained in the collapsed state by the catheter body, and wherein relative movement between the catheter body and the embolic filter in a first direction enables the embolic filter to move from the collapsed state to the deployed state.

The delivery catheter assembly may comprise a deflecting member attached to an internal surface of the catheter and to a control member. The control member may be configured to manipulate the deflecting member so as to adjust the position of the catheter within the vasculature of a patient, in use.

By providing an arrangement capable of deflecting the external catheter, the internal catheter can be centralized in the vessel of a patient, which centralizes the prosthesis delivery catheter. This can advantageously reduce contact with the vessel wall and/or help with deployment of an article.

The embolic filter may be connected to the internal catheter at or near a distal tip thereof.

The catheter may comprise an elongate catheter body having a distal tip and a capsule containing a deliverable prosthesis, and the embolic filter may be connected to the catheter proximal to the capsule.

The embolic filter may be connected to the internal catheter by adhesive, sewing, crimping or thermobonding.

The embolic filter may be connected to a releasable fastener that is configured to releasably engage the catheter so as to releasably attach the embolic filter to the catheter.

The delivery catheter assembly may be configured such that relative movement between the catheter and the capsule in the first direction beyond a predetermined distance causes the releasable fastener to disengage from the capsule.

The delivery catheter assembly may be configured such that relative movement between the catheter and the capsule in a second, retraction, direction beyond a predetermined distance causes the releasable fastener to engage from capsule.

The embolic filter may be connected to a resilient fastener, e.g. a c-clip or coil.

The resilient fastener may be urged into engagement with an external surface of the capsule in a first, e.g. retracted, position so as to releasably attach the embolic filter to the internal catheter.

The resilient fastener may expand into an internal groove on the catheter in a second, e.g. advanced, position such that the resilient fastener disengages from the capsule to enable the capsule to be advanced independently of the embolic filter.

The catheter may comprise an abutment surface configured and arranged to abut against the resilient fastener when the catheter from a position beyond the second, advanced, position past said second, advanced position so as to move the resilient fastener along a tapered surface of the internal groove so as to be urged into engagement with an external surface of the capsule and releasably attach the embolic filter to the capsule.

Relative movement between the catheter and the capsule in a second direction, opposite to the first direction, may move the embolic filter from the deployed state to the collapsed state.

The embolic filter may comprise a support frame, e.g. a nitinol support frame, and a porous polymeric membrane covering the support frame.

The support structure may comprise a shape memory material such that the support frame acts as a deployment arrangement to move the embolic filter from the collapsed state into the deployed state.

The porous polymeric membrane may be a biocompatible fabric comprising a pore size of between 100 and 200 nanometers.

According to a second aspect of the invention there is provided an introducer device comprising: an introducer sheath, wherein the catheter is arranged, e.g. substantially coaxially, within the introducer sheath, in use.

The advantage of this arrangement is that it helps to avoid the need for having two catheters in parallel in the vessel which could lead to interaction and bring complications during the procedure.

The introducer device may comprise a control member, e.g. a handle or rotatable collar, to actuate movement of introducer sheath relative to catheter.

BRIEF DESCRIPTION OF DRAWINGS

Embodiments of the present invention will now be described with reference to the accompanying figures in which:

FIGS. 2 and 3 show side views of a delivery catheter system according to an embodiment of the present invention;

FIGS. 9 and 10 show side views of an introducer device according to the present invention;

DETAILED DESCRIPTION

Figure 1:
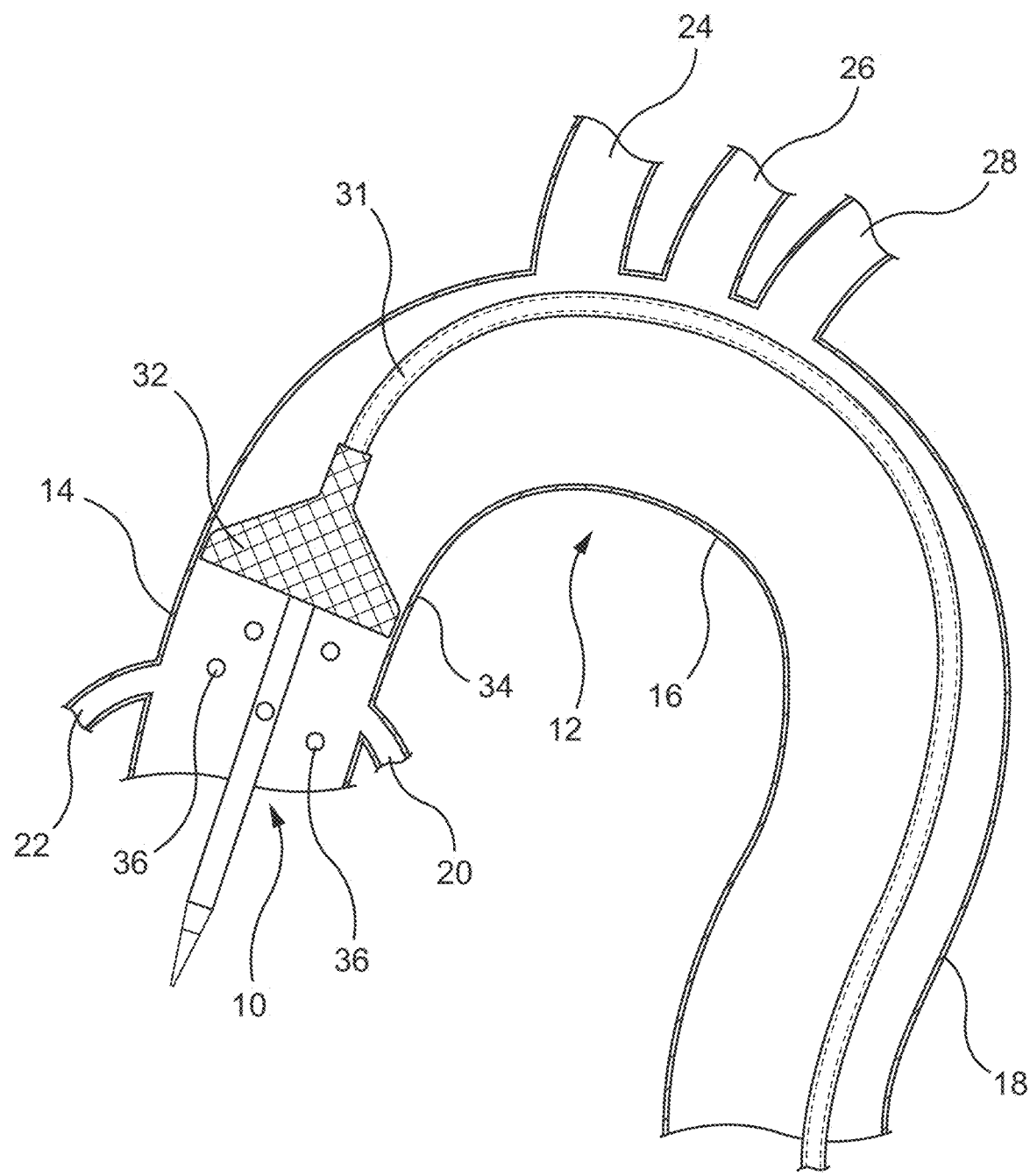
FIG. 1 shows a side view of a TAVI delivery catheter and embolic filter located within the aorta of a patient

Referring firstly to FIG. 1 there is shown components of a delivery catheter system generally designated 10 located within the aorta 12 of a patient. The features of the aorta include the ascending aorta 14, the arch of aorta 16, the descending aorta 18, the left and right coronary arteries 20, 22, the brachiocephalic artery 24, the left common carotid artery 26 and the left subclavian artery 28. Not shown is the aortic valve which is to be replaced.

The delivery catheter system 10 includes catheter 30 and an embolic filter 32. In the illustrated embodiment, the catheter may be considered to be a TAVI delivery catheter, and the embodiment is described with reference to a TAVI procedure. It will be appreciated, however, that in alternative embodiments the catheter may be used for different valve replacement procedures, or may be used in the placement of an intravascular stent.

The TAVI delivery catheter 30 may, by way of illustrative example only, correspond to the Medtronic EnVeo PRO™ delivery catheter system. The TAVI delivery catheter 30 includes an elongate catheter body 31 having a distal tip 33. The TAVI delivery catheter 30 further includes a capsule (not shown) containing a replacement valve. The filter 32 is provided circumferentially around an outer surface of the TAVI delivery catheter 30 and extends across the annulus defined the between the TAVI delivery catheter 30 and the wall 34 of the ascending aorta 14. The filter 32 is configured so as to be able to conform to the wall 34 of the ascending aorta 14 and thus provide required sealing characteristics against the wall of ascending aorta 14. The filter 32 is provided with a high porosity membrane that doesn't restrict blood flow but at the same time provides the desired filtering characteristics to capture any debris 36 that may be dislodged by the TAVI procedure.

In the embodiment shown, the filter 32 is positioned in the ascending aorta 14 downstream of the left and right coronary arteries 20, 22 and upstream of the arch of aorta 16. Any debris 36 that may be dislodged by the TAVI procedure is thus captured by the filter 32 and prevented from reaching and entering the brachiocephalic artery 24, the left common carotid artery 26 and/or the left subclavian artery 28. It will be appreciated that the filter 32 may alternatively be positioned in the arch of the aorta 14 and downstream of the left and right coronary arteries 20, 22 and upstream of the brachiocephalic artery 24, the left common carotid artery 26 and/or the left subclavian artery 28. In some arrangements, it will be appreciated that the filter 32 may be arranged downstream of the left and right coronary arteries 20, 22 in the arch of the aorta 14 so as to cover the brachiocephalic artery 24, the left common carotid artery 26 and/or the left subclavian artery 28.

It will be appreciated that FIG. 1 shows the filter 32 in a deployed state. The filter 32 is initially provided in an un-deployed or collapsed state. Although not illustrated, TAVI delivery catheter 30 and the collapsed filter 32 may be covered by an external catheter. The external catheter acts as a sheath or sleeve that maintains the filter 32 in the collapsed state during advancement of the TAVI delivery catheter 30 through the vasculature of the patient. Upon delivery of the replacement valve, i.e. upon positioning of the replacement valve in the desired location within the aorta 12 of a patient, the filter 32 can be moved to the deployed state. This may be achieved by, for example, by relative movement between the TAVI delivery catheter 30 and the external catheter in a first direction so as to uncover the filter 32. The filter 32 may then move from the collapsed state to the deployed state, for example via shape memory material portions of the filter 32.

The embolic filter 32 is formed from a support frame 38. The support frame 38 may be formed from a shape memory material, for example a shape memory alloy or shape memory polymer. In each of the embodiments discussed herein, the shape memory material is nitinol, but it will be appreciated that any suitable shape memory material may be used. The filter 32 also includes a porous polymeric membrane 40 covering the support frame. The polymeric membrane 40 may comprise a biocompatible porous fabric having a pore size of between 100 and 200 nanometers.

With the filter 32 deployed and extending across the aforementioned annulus between the TAVI delivery catheter 30 and the wall 34 of the ascending aorta 14, the TAVI procedure can be conducted. As noted above, any debris 36 that is be dislodged by the TAVI procedure is thus captured by the filter 32 and prevented from reaching and entering the brachiocephalic artery 24, the left common carotid artery 26 and/or the left subclavian artery 28. Once the TAVI procedure has been completed, and prior to the withdrawal of the TAVI delivery catheter 30 from the vasculature of the patient, the filter 32 is retrieved or moved back to its un-deployed or collapsed state from its deployed state while still retaining any debris 36 that may have been collected. Movement of the filter 32 back to its un-deployed or collapsed state from its deployed state may be achieved by, for example manipulation or movement of the sheath or sleeve back to its initial position.

Once the TAVI procedure has been completed, and prior to the withdrawal of the delivery catheter 30 from the vasculature of the patient, the filter 32 is retrieved while still retaining any debris 36 that may have been collected. Put another way, the filter 32 is moved back to its un-deployed or collapsed state from its deployed state while still retaining any debris 36 that may have been collected. Movement of the filter 32 back to its un-deployed or collapsed state from its deployed state may be achieved by relative movement between the TAVI delivery catheter 30 and the external catheter in a second direction, opposite to the first direction. Put another way, movement of the filter 32 back to its un-deployed or collapsed state from its deployed state may be achieved by movement of the sheath back to its initial position.

Referring now to FIGS. 2 and 3 there is shown an embodiment of a delivery catheter system generally designated 110.

The delivery catheter system 110 includes a catheter 30 having an elongate body. Although not illustrated, the catheter 30 may be positioned within an introducer sheath of a delivery device. An embolic filter 32 is integrated with the catheter 30. The embolic filter 32 is deployable from the catheter 30 prior to the delivery of an article or prosthesis in a patient's vasculature and retrievable to the catheter 30 after delivery of said article. It will be appreciated that the delivery catheter system 110 may be used for a range of different purposes, and the article or prosthesis being delivered will vary accordingly. The delivery catheter system 110 may be used to deliver a replacement valve place a stent in a patient's vasculature, and as such the article may be a valve or a stent, for example.

In the arrangement shown, the embolic filter 32 is connected to a releasable fastener 56. The releasable fastener 56 is configured to releasably engage the catheter 30 so as to releasably attach the embolic filter 32 to the capsule 35.

Relative movement between the catheter 30 and the capsule 35 in a first direction, e.g. a retraction of the catheter 30, enables the embolic filter 32 to move from a collapsed state, whereupon the embolic filter 32 is retained closely to the body 31 of the catheter 30, to a deployed state where the embolic filter 32 extends from the body 31 of the catheter 30 and, in use, into contact with an inner wall of a patient's vasculature. The filter 32 may then move from the collapsed state to the deployed state, for example via one or more shape memory portions of the filter 32. The support frame 38 may be formed from a shape memory material, for example a shape memory alloy or shape memory polymer. In each of the embodiments discussed herein, the shape memory material is nitinol, but it will be appreciated that any suitable shape memory material may be used. The filter 32 also includes a porous polymeric membrane 40 covering the support frame. The polymeric membrane 40 may comprise a biocompatible porous fabric having a pore size of between 100 and 200 nanometers.

The delivery catheter system 110 is configured such that relative movement between the catheter 30 and the capsule 35 in a first direction beyond a predetermined distance causes the releasable fastener 56 to disengage from the capsule 35. Put another way, the delivery catheter system 110 is configured such that retraction of the catheter 30 and/or advancement of the capsule 35 beyond a predetermined distance causes the releasable fastener 56 to disengage from the capsule 35.

The delivery catheter system 110 is configured such that relative movement between the catheter 30 and the capsule 35 in a second direction, opposite to the first direction, beyond a predetermined distance causes the releasable fastener 56 to engage the capsule 35. Put another way, the delivery catheter system 110 is configured such that extension/advancement of the catheter 30 and/or retraction of the capsule 35 beyond a predetermined distance causes the releasable fastener 56 to engage from the capsule 35.

In the arrangement shown, the embolic filter 32 is connected to a resilient fastener 56, e.g. a resilient clip such as a c-clip or a resilient coil. The resilient fastener 56 is urged into engagement with the body of the capsule 35 in a first, e.g. retracted, position. Urging of the resilient fastener 56 into engagement with the capsule 35 works to releasably attach the embolic filter 32 to the capsule 35. In a second, e.g. advanced, position, the resilient fastener 56 expands into an internal groove 58 on the catheter 30. This results in the resilient fastener 56 disengaging from the capsule 35. At this point the embolic filter 32 is completely deployed. Disengaging or decoupling of the resilient fastener 56 (i.e. the embolic filter 32) when the embolic filter 32 is deployed enables the capsule 35 to be advanced independently of the embolic filter 32.

When the capsule 35 is retracted, it abuts against the resilient fastener 56. The catheter 30 comprises an abutment surface 60 configured and arranged to abut against the resilient fastener 56 when the catheter 30 is retracted from a position beyond the second, advanced, position past said second, advanced position. The abutment surface 60 moves the resilient fastener 56 along a tapered surface 62 of the internal groove 58 so as to be urged into engagement with the capsule 35. This works to releasably attach the embolic filter 32 to the capsule 35. This, in turn, enables all of the delivery catheter system 110 to be removed from a patient.

The embodiment of FIGS. 2 and 3 ensures that the embolic filter 32 is deployed before delivery of an article, e.g. a valve prosthesis. Put another way, the embodiment of FIGS. 2 and 3 ensures that the embolic filter 32 is deployed before the capsule 35 is advanced. Following deployment of the embolic filter 32, the capsule 35 can then be moved back and forward without limitations. In that way it doesn't change the way a procedure is usually made. The capsule 35 can move forward independently, but when the capsule 35 is retracted, it also urges the resilient fastener 56 into engagement with the capsule 35.

The delivery catheter system 110 includes a deflecting member 45. The deflecting member 45 is attached to an internal surface of the catheter 30. The deflecting member 45 is configured to adjust the position of the catheter 30 (i.e. of the distal tip 33) within the vasculature of a patient. It will be appreciated that although not illustrated, the deflecting member 45 may be utilised any of the delivery catheter systems illustrated in FIGS. 4 to 8 and or may be utilised in the introducer sheath of the introducer device illustrated in FIGS. 9 to 12.

Although not illustrated, the deflecting member is attached to a control member (e.g. a handle or collar of a delivery device or another device) so as to be controlled by a physician to steer the external catheter within a patient's vasculature. The control member is configured to manipulate the deflecting member 45 so as to adjust the position of the catheter 30 within the vasculature of a patient, in use.

In the arrangement shown, the deflecting member is elongate wire, but it will be appreciated that any suitable arrangement for adjusting the position of the catheter 30 (i.e. of the distal tip 33) within the vasculature of a patient may be used. The deflecting member 45 may be provided within a cover, e.g. an elongate tubular cover, within the catheter 30.

The deflecting member may be attached, e.g. welded, to the catheter 30. In such arrangements, it will be appreciated that the deflecting member 45 will be positioned within the catheter 30 so as to not to interfere with the embolic filter 32 e.g. when the embolic filter is in the collapsed state within the external catheter. Put another way, it will be appreciated that the deflecting member 45 will be attached (and terminate) at a position within the catheter 30 so as to not to interfere with the embolic filter 32 e.g. when the embolic filter is in the collapsed state within the external catheter.

Figure 4:
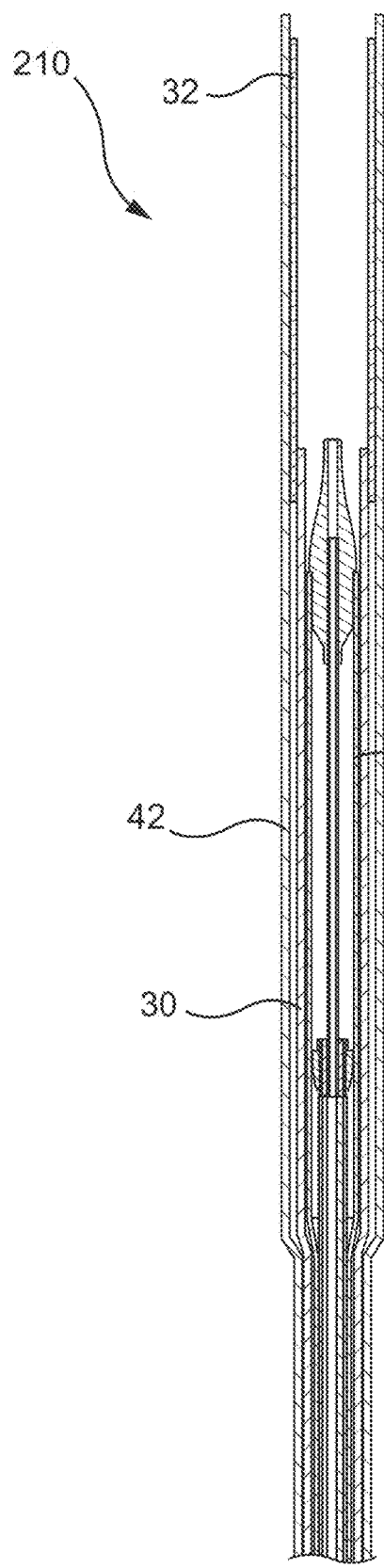
FIGS. 4 and 5 shows side views of a delivery catheter system according to another embodiment of the present invention.
Figure 5:
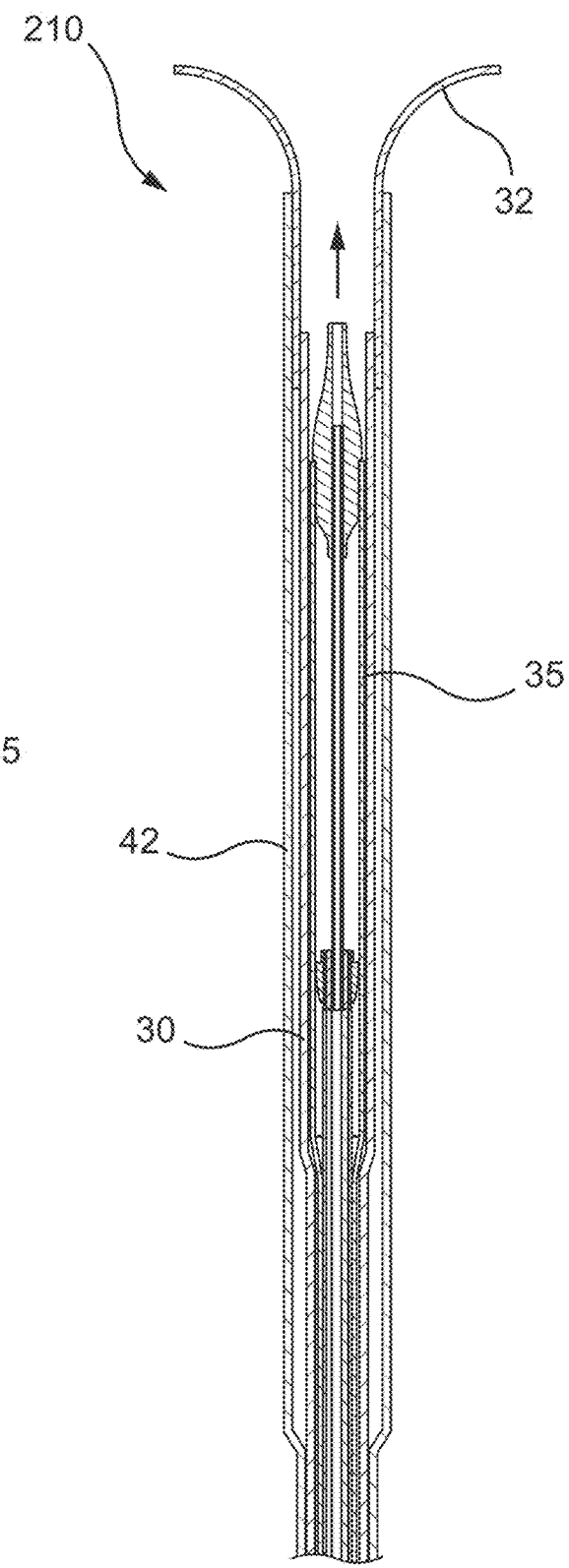

Referring now to FIGS. 4 and 5 there is shown an embodiment of a delivery catheter system generally designated 210.

The delivery catheter system 210 includes a catheter 30 having an elongate body. In the arrangement shown, the catheter 30 is positioned within an external tube or catheter 42. It will be understood that the external tube or catheter may be an introducer sheath 42 of an introducer device (as is discussed in more detail below). The introducer sheath 42 has an elongate body. The catheter 30 is positioned within the elongate body of the introducer sheath 42. An embolic filter 32 is integrated with the catheter 30. The embolic filter 32 is deployable from the introducer sheath 42 prior to the delivery of an article in a patient's vasculature and retrievable to the introducer sheath 42 after delivery of said article. It will be appreciated that the delivery catheter system 210 may be used for a range of different purposes, and the article being delivered will vary accordingly. The delivery catheter system may be used to place a replacement valve or a stent in a patient's vasculature, and as such the article may be a valve or a stent, for example. The delivery catheter system may be used for a transcatheter aortic valve implantation, and as such the article may be a replacement valve. Alternatively, the delivery catheter system may be used for any suitable purpose.

Relative movement between the introducer sheath (i.e. an external catheter) 42 and the catheter 30 in a first direction, e.g. a retraction of the introducer sheath 42, enables the embolic filter 32 to move from a collapsed state, whereupon the embolic filter 32 is retained closely to the body of the catheter 30, to a deployed state where the embolic filter 32 extends from the body 31 of the catheter 30 and, in use, into contact with an inner wall of a patient's vasculature. The filter 32 may then move from the collapsed state to the deployed state, for example via one or more shape memory portions of the filter 32. The support frame 38 may be formed from a shape memory material, for example a shape memory alloy or shape memory polymer. In each of the embodiments discussed herein, the shape memory material is nitinol, but it will be appreciated that any suitable shape memory material may be used. The filter 32 also includes a porous polymeric membrane 40 covering the support frame. The polymeric membrane 40 may comprise a biocompatible porous fabric having a pore size of between 100 and 200 nanometers.

In the embodiment shown, the introducer sheath 42 is configured (i.e. sized) to be capable of receiving a delivery catheter system (i.e. a catheter 30) therethrough. The delivery catheter system 30 may be a transcatheter aortic valve implantation (TAVI) delivery catheter, a stent delivery catheter, a tool delivery catheter, or may delivery any other valve to a patient.

The catheter 30 has an elongate catheter body 31 having a distal tip 33 and a capsule 35 containing a deliverable article such as a stent or a replacement valve. The embolic filter 32 is connected to the catheter 30 at or near a distal tip 33 thereof. The embolic filter 32 may be connected to the catheter 30 by adhesive, sewing, crimping, thermobonding or any other suitable attachment arrangement. In the arrangement shown, the embolic filter 32 is positioned distal to (i.e. on the distal side of) the capsule 35, when the capsule 35 is in the retracted position. Put another way, when the capsule 35 is in the retracted position, the capsule 35 is positioned within the catheter 30. When the capsule 35 is in the retracted position, the capsule 35 is positioned within the introducer sheath 42.

With the filter 32 deployed and extending across the aforementioned annulus between the catheter 30 and the wall 34 of the aorta 14, the capsule 35 is advanced along the patient's vasculature so that the procedure can be conducted. Any debris 36 that is be dislodged by the procedure is thus captured by the filter 32 and prevented from reaching and entering the descending aorta 18, brachiocephalic artery 24, the left common carotid artery 26 and/or the left subclavian artery 28.

Once the procedure has been completed, the article catheter 30 is retrieved. Prior to the withdrawal of the external catheter 42 from the vasculature of the patient, the filter 32 is retrieved while still retaining any debris 36 that may have been collected. Put another way, the filter 32 is moved back to its un-deployed or collapsed state from its deployed state while still retaining any debris 36 that may have been collected. Movement of the filter 32 back to its un-deployed or collapsed state from its deployed state may be achieved by relative movement between the external catheter 42 and the catheter 30 in a second direction, opposite to the first direction. This movement may be considered to be an extension or advancement of the external catheter 42. Put another way, movement of the filter 32 back to its un-deployed or collapsed state from its deployed state may be achieved by movement of the external catheter 42 back to its initial position.

Figure 6:
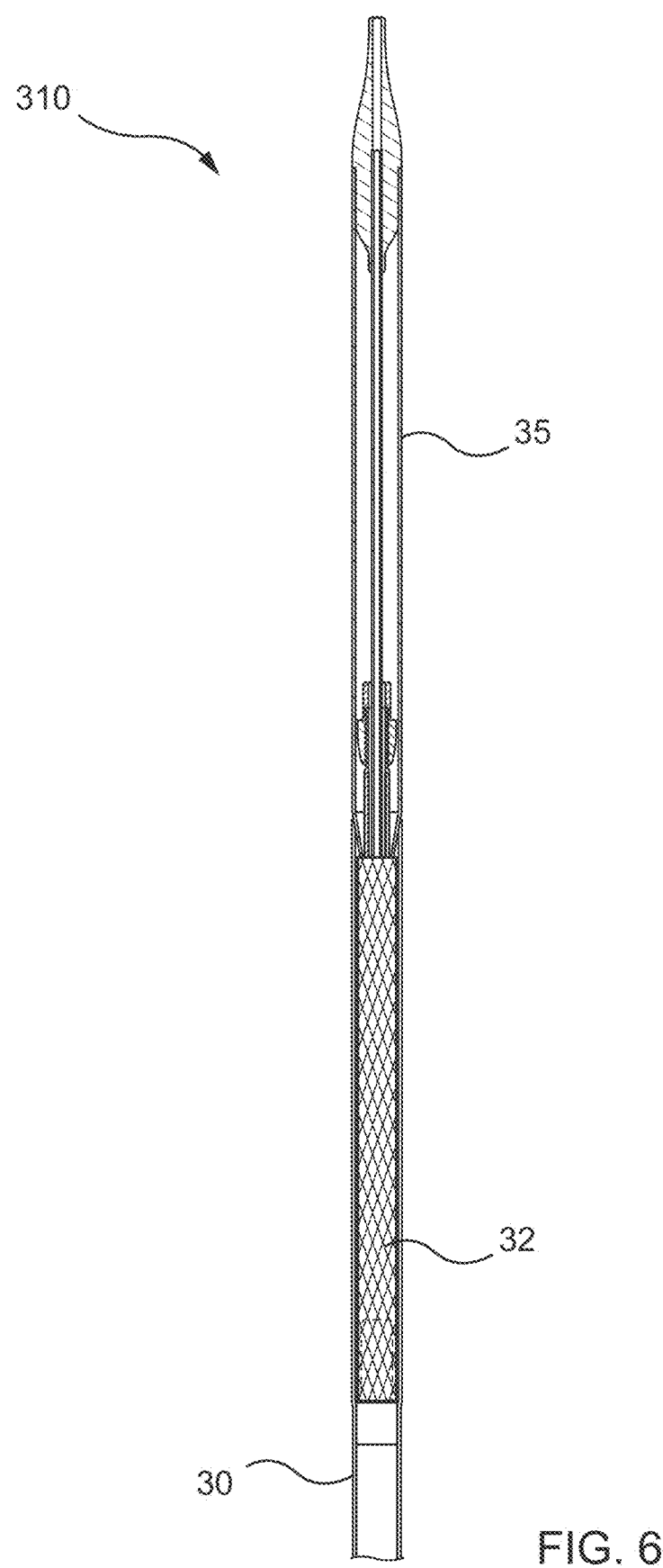
FIGS. 6, 7 and 8 shows side views of a delivery catheter system according to another embodiment of the present invention.
Figure 7:
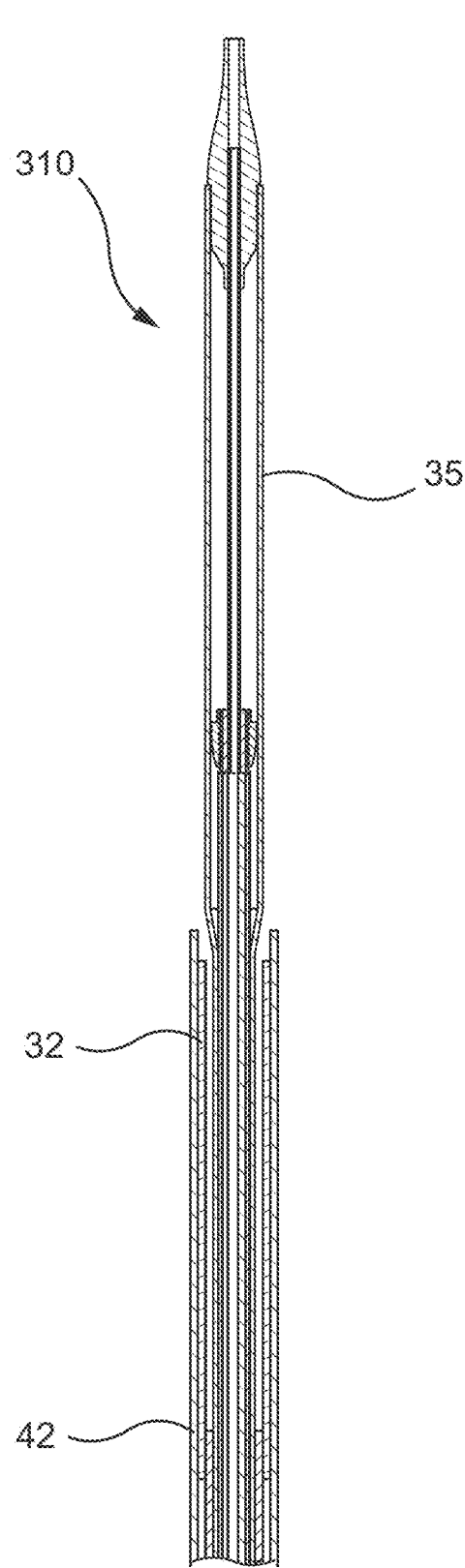
Figure 8:
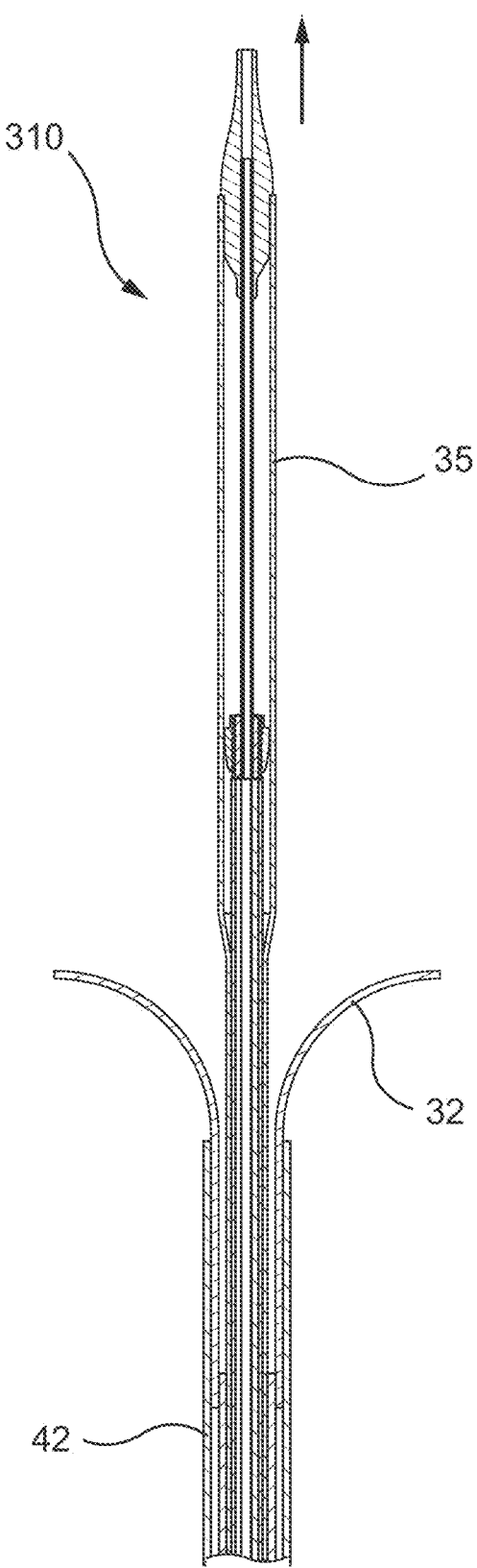

Referring now to FIGS. 6 to 8 there is shown an embodiment of a delivery catheter system generally designated 310.

The delivery catheter system 310 includes a catheter 30 having an elongate body. The delivery catheter system 310 includes an internal catheter having an elongate body. In the arrangement shown, the catheter 30 is positioned within an external tube or catheter 42. It will be understood that the external tube or catheter may be an introducer sheath 42 of an introducer device (as is discussed in more detail below). The introducer sheath 42 has an elongate body. The catheter 30 is positioned within the elongate body of the introducer sheath 42.

An embolic filter 32 is integrated with the catheter 30. The embolic filter 32 is deployable from the introducer sheath 42 prior to the delivery of an article in a patient's vasculature and retrievable to the introducer sheath 42 after delivery of said article. It will be appreciated that the delivery catheter system 310 may be used for a range of different purposes, and the article being delivered will vary accordingly. The delivery catheter system may be used to place a replacement valve or a stent in a patient's vasculature, and as such the article may be a valve or a stent, for example. The delivery catheter system may be used for a transcatheter aortic valve implantation, and as such the article may be a replacement valve. Alternatively, the delivery catheter system may be used for any suitable purpose.

Relative movement between the introducer sheath (i.e. an external catheter) 42 and the catheter 30 in a first direction, e.g. a retraction of the introducer sheath 42, enables the embolic filter 32 to move from a collapsed state, whereupon the embolic filter 32 is retained closely to the body of the catheter 30, to a deployed state where the embolic filter 32 extends from the body of the catheter 30 and, in use, into contact with an inner wall of a patient's vasculature. The filter 32 may then move from the collapsed state to the deployed state, for example via one or more shape memory portions of the filter 32. The support frame 38 may be formed from a shape memory material, for example a shape memory alloy or shape memory polymer. In each of the embodiments discussed herein, the shape memory material is nitinol, but it will be appreciated that any suitable shape memory material may be used. The filter 32 also includes a porous polymeric membrane 40 covering the support frame. The polymeric membrane 40 may comprise a biocompatible porous fabric having a pore size of between 100 and 200 nanometers.

In the embodiment shown, the introducer sheath 42 is configured (i.e. sized) to be capable of receiving a delivery catheter system (i.e. a catheter 30) therethrough. The delivery catheter system may be a transcatheter aortic valve implantation (TAVI) delivery catheter, a stent delivery catheter, a tool delivery catheter, or may delivery any other valve to a patient.

The catheter 30 has an elongate catheter body 31 having a distal tip 33 and a capsule 35 containing a deliverable article such as a stent or a replacement valve. The embolic filter 32 is connected to the catheter 30 at or near the distal tip 33 thereof. The embolic filter 32 may be connected to the catheter 30 by adhesive, sewing, crimping, thermobonding or any other suitable attachment arrangement.

In the arrangement shown, the embolic filter 32 is connected to the delivery catheter 30 proximal to (i.e. on a proximal or downstream side of) the capsule 35, when the capsule 35 is in the retracted position. Put another way, when the capsule 35 is in the retracted position, the capsule 35 protrudes from the catheter 30 and the introducer sheath 42.

In this arrangement, the external catheter 42 and the delivery catheter 30 do not extend over the capsule 35. Put another way, the capsule 35 is oversized relative to the delivery catheter 30 such that the capsule 35 cannot extend along said delivery catheter 30. This arrangement enables the diameter of the delivery catheter system 310, i.e. the external catheter 42, to be substantially equal to the external diameter of the capsule 35.

Once the procedure has been completed, the article catheter 30 is retrieved. Prior to the withdrawal of the external catheter 42 from the vasculature of the patient, the filter 32 is retrieved while still retaining any debris 36 that may have been collected. Put another way, the filter 32 is moved back to its un-deployed or collapsed state from its deployed state while still retaining any debris 36 that may have been collected. Movement of the filter 32 back to its un-deployed or collapsed state from its deployed state may be achieved by relative movement between the external catheter 42 and the catheter 30 in a second direction, opposite to the first direction. This movement may be considered to be an extension or advancement of the external catheter 42. Put another way, movement of the filter 32 back to its un-deployed or collapsed state from its deployed state may be achieved by movement of the external catheter 42 back to its initial position.

Referring now to FIGS. 9 to 12 there is shown an embodiment of an introducer device 48.

The introducer device 48 includes an introducer sheath 42. The introducer sheath 42, or external catheter, holds the vessel (i.e. the vasculature of a patient) open so as to enable practitioners to insert other tools safely into the area of interest. Instead of inserting each tool within the skin opening, the tools are removed and inserted via the introducer sheath which minimizes the blood loss, minimizes skin damage and helps to deliver the tools at the right location. It will be appreciated that the introducer device 48 may be used in combination with any of the delivery catheter systems illustrated in FIGS. 1 to 8.

The introducer device 48 includes a control member 50. The control member 50 is provided to actuate movement (i.e. extension and retraction) of the introducer sheath 42 relative to the catheter 30. The control member 50 may be provided in the form of a handle or collar 52 that is rotatable so as to actuate movement of the introducer sheath 42 relative to the catheter 30. In alternative arrangements, however, it will be appreciated that any suitable control member may be provided to actuate movement of the introducer sheath 42 relative to the catheter 30.

The introducer device 48 includes an upstream inlet 54 for receiving a catheter 30 therein to enable said catheter 30 to be delivered (i.e. positioned) at the desired location. Although not illustrated, the delivery device 48 and/or the introducer sheath 42 may be provided with a valve arrangement to prevent the leakage of blood from the inlet 54.

The introducer device includes an embolic filter 32 deployable from a distal end of the introducer sheath 42, as shown in FIG. 10. The embolic filter 32 may be deployable from the introducer sheath 42 as disclosed above.

Figure 11:
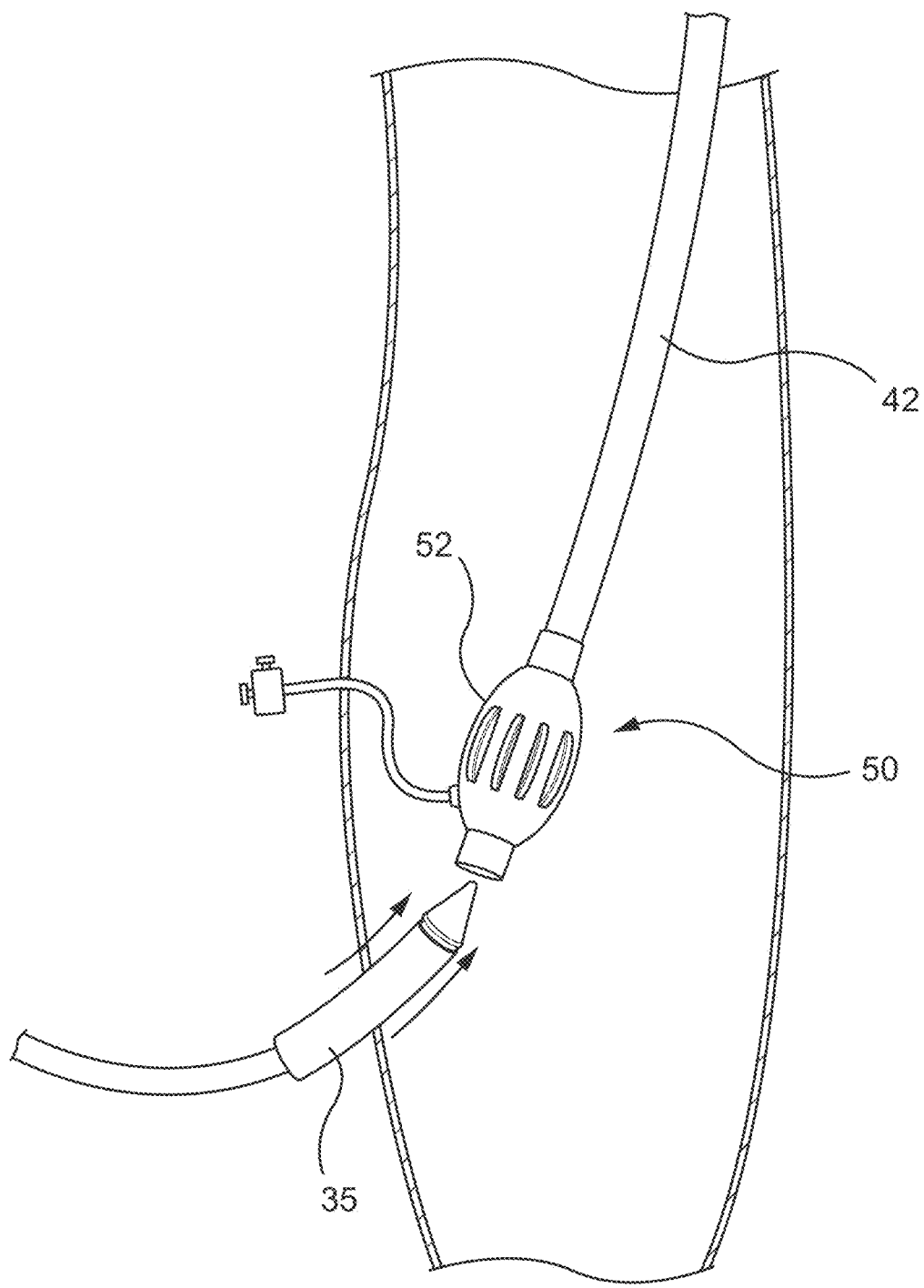
FIG. 11 shows the manner in which the delivery catheter system is introduced into the introducer device.
Figure 12:
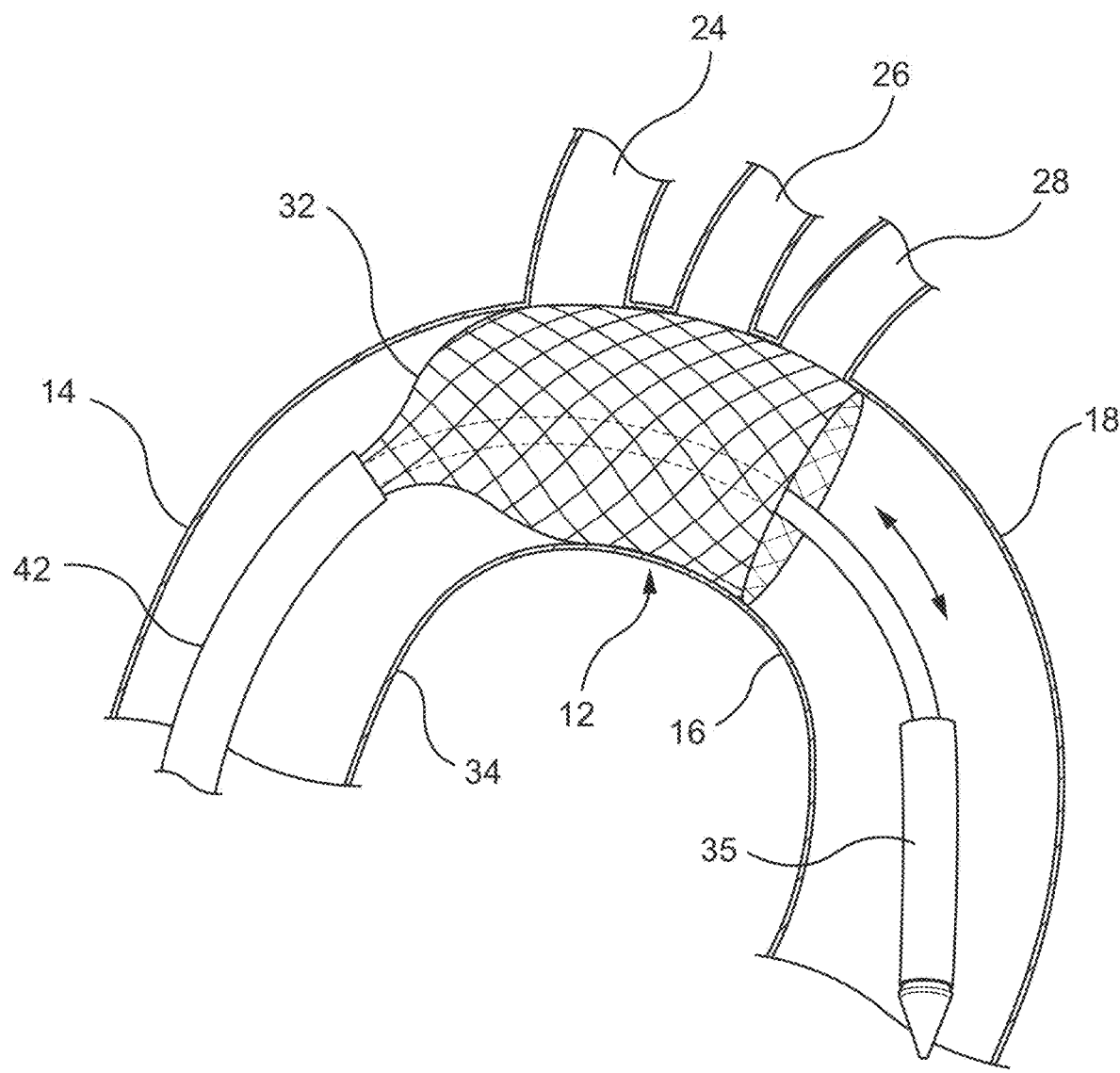
FIG. 12 shows the manner in which the catheter exits the distal end of the introducer device.

FIG. 11 shows the introducer device 48 inserted in the femoral access. Once the introducer sheath 42 has been inserted, and the embolic filter 32 has been deployed, a catheter 30 can be advanced so as to protrude from the distal tip 46 of the introducer sheath 42 (as is illustrated in FIG. 8). It will be appreciated that any kind of catheter 30 can be inserted through the introducer device 48. The introducer sheath 42 is able to remain in a patient's vasculature such that several tools can be brought to the annulus. For example, if a valve prosthesis (such as an aortic valve prosthesis) has been wrongly released, the catheter 30 can be removed and a second catheter 30 can be inserted while the introducer sheath 42 stays in position in the vasculature of the patient.

The invention claimed is:

1. A delivery catheter system comprising:
   a catheter including an elongate catheter body having a distal tip and a capsule containing a deliverable prosthesis;
   an integrated embolic filter, the embolic filter deployable prior to the delivery of a prosthesis in a patient's vasculature and retrievable after delivery of said prosthesis; and
   a deflecting member connected to an internal surface of the catheter body and to a control member, wherein the control member is configured to manipulate the deflecting member so as to adjust the position of the distal tip within the vasculature of a patient, in use, wherein the embolic filter is moveable from a collapsed state, in which the embolic filter is retained within the catheter body, to a deployed state in which the embolic filter extends from the catheter body and, in use, into contact with an inner wall of a patient's vasculature.

2. A delivery catheter system according to claim 1, wherein the embolic filter is retained in the collapsed state by the catheter body, and wherein relative movement between the catheter body and the embolic filter in a first direction enables the embolic filter to move from the collapsed state to the deployed state.

3. A delivery catheter system according to claim 2, wherein relative movement between the catheter body and the embolic filter in a second direction, opposite to the first direction, moves the embolic filter from the deployed state to the collapsed state.

4. A delivery catheter system according to claim 1, wherein the embolic filter is connected to the catheter at or near the distal tip.

5. A delivery catheter system according to claim 4, wherein the embolic filter is connected proximal to the capsule.

6. A delivery catheter system according to claim 4, wherein the embolic filter is attached to the catheter by adhesive, sewing, crimping and/or thermobonding.

7. A delivery catheter system according to claim 1, wherein the embolic filter is connected to a releasable fastener releasably engaged to the capsule so as to releasably attach the embolic filter to the capsule.

8. A delivery catheter system according to claim 1, wherein the embolic filter is connected to a resilient fastener, and wherein said resilient fastener is urged into engagement with an external surface of the capsule in a first, retracted, position so as to releasably attach the embolic filter to the capsule.

9. A delivery catheter system comprising:
- a catheter including an elongate catheter body having a distal tip and a capsule containing a deliverable prosthesis; and
- an integrated embolic filter, the embolic filter deployable prior to the delivery of a prosthesis in a patient's vasculature and retrievable after delivery of said prosthesis,
- wherein the embolic filter is moveable from a collapsed state, in which the embolic filter is retained within the catheter body, to a deployed state in which the embolic filter extends from the catheter body and, in use, into contact with an inner wall of a patient's vasculature,
- wherein the embolic filter is connected to a releasable fastener that is releasably engaged to the capsule so as to releasably attach the embolic filter to the capsule,
- wherein relative movement between the catheter body and the capsule in a first direction beyond a predetermined distance causes the releasable fastener to disengage from the capsule.

10. A delivery catheter system according to claim 9, wherein relative movement between the catheter body and the capsule in a second, retraction, direction beyond a predetermined distance causes the releasable fastener to engage the capsule.

11. A delivery catheter system comprising;
- a catheter including an elongate catheter body having a distal tip and a capsule containing a deliverable prosthesis; and
- an integrated embolic filter, the embolic filter deployable prior to the delivery of a prosthesis in a patient's vasculature and retrievable after delivery of said prosthesis,
- wherein the embolic filter is moveable from a collapsed state, in which the embolic filter is retained within the catheter body, to a deployed state in which the embolic filter extends from the catheter body and, in use, into contact with an inner wall of a patient's vasculature,
- wherein the embolic filter is connected to a resilient fastener, and wherein said resilient fastener is urged into engagement with an external surface of the capsule in a first, retracted, position so as to releasably attach the embolic filter to the capsule,
- wherein the resilient fastener expands into an internal groove on the catheter body in a second, advanced, position such that the resilient fastener disengages from the capsule to enable the capsule to be advanced independently of the embolic filter.

12. A delivery catheter system according to claim 11, wherein the catheter body comprises an abutment surface configured and arranged to abut against the resilient fastener when the capsule is retracted from a position beyond the second, advanced, position past said second, advanced, position so as to move the resilient fastener along a tapered surface of the internal groove to urge the resilient fastener into engagement with capsule.

* * * * *